(12) United States Patent
Nakajima et al.

(10) Patent No.: US 8,409,094 B2
(45) Date of Patent: Apr. 2, 2013

(54) ULTRASOUND DIAGNOSTIC APPARATUS AND METHOD FOR DISPLAYING ULTRASOUND IMAGE

(75) Inventors: Osamu Nakajima, Tochigi-ken (JP); Jiro Higuchi, Tochigi-ken (JP); Kazuya Akaki, Tochigi-ken (JP); Takayuki Gunji, Tochigi-ken (JP); Koichiro Kurita, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 601 days.

(21) Appl. No.: 11/686,028

(22) Filed: Mar. 14, 2007

(65) Prior Publication Data

US 2007/0239008 A1    Oct. 11, 2007

(30) Foreign Application Priority Data

Mar. 15, 2006  (JP) .................. P2006-71041

(51) Int. Cl.
*A61B 8/00*   (2006.01)
(52) U.S. Cl. ..................................... 600/437; 600/407
(58) Field of Classification Search .................. 600/437, 600/407
See application file for complete search history.

(56) References Cited

U.S. PATENT DOCUMENTS 6,669,641 B2 * 12/2003 Poland et al. .................. 600/447
2006/0004291 A1 * 1/2006 Heimdal et al. .............. 600/459

* cited by examiner

*Primary Examiner* — Unsu Jung
*Assistant Examiner* — Rajeev Siripurapu
(74) *Attorney, Agent, or Firm* — Oblon, Spivak, McClelland, Maier & Neustadt, L.L.P.

(57) ABSTRACT

An ultrasound diagnostic apparatus including a transmitting and receiving unit configured to transmit and receive ultrasound waves and from a plurality of planes of a subject by an ultrasonic probe, and an image signal generation unit configured to execute image processing on the basis of received signal from the transmitting and receiving unit and to generate image signals for ultrasound images indicating each of the planes, wherein the transmitting and receiving unit or the image signal generation unit as configured to execute transmitting and receiving or image processing with respect to one of the planes in a condition that is different with respect to another of the planes.

17 Claims, 7 Drawing Sheets

movie    movie

Fig. 4(b)

freeze    movie

rough     dense

ULTRASOUND DIAGNOSTIC APPARATUS AND METHOD FOR DISPLAYING ULTRASOUND IMAGE

CROSS-REFERENCE TO RELATED APPLICATIONS

This application is based upon and claims the benefit of priority from the prior Japanese Patent Application No. 2006-71041, filed on Mar. 15, 2006, the entire contents of which are incorporated herein by reference.

BACKGROUND OF THE INVENTION

Field of the Invention

An ultrasound diagnostic apparatus having a multi plane scan function is known in the art. Such an ultrasound diagnostic apparatus is used with a two dimensional arrayed probe or mechanical oscillation probe configured to transmit ultrasound beams to a universal direction. For the usage of such a probe, a plurality of planes of a subject can be scanned at essentially the same time. Therefore, for such a scanning, a plurality of ultrasound images indicating different planes of the subject are displayed alongside one another. This function is called a multi plane scan function or multi display function. By observing ultrasound images produced in conjunction with this function, a doctor can make a diagnosis on the basis of a 3 dimensional understanding of the subject.

In the ultrasound diagnostic apparatus having a multi plane scan function or multi display function, a variety of imaging conditions or displaying conditions can be employed. The imaging conditions to be selected include ultrasound power, scanning line density, receiving sensitivity, signal processing and so on. The display conditions include display size, display scanning line density and so on. The plurality of ultrasound images is generated on the basis of the same imaging conditions and displaying conditions. The ultrasound images then each have a same image quality.

By the way, because the observable viewing range is not so broad, in spite of displaying a plurality of images, the number of images which one can observe at one time is limited to about one. In this case, because an ultrasound image that is not being observed has a meaning as a pilot image, there is often a case that a doctor need not observe one ultrasound image closely.

However, in the hitherto known ultrasound diagnostic apparatus, when a doctor wants to observe one of displayed images closely, the doctor must adjust imaging conditions or displaying conditions of all images displayed at the same time. For example, when scanning line density and display size is changed into high values, the condition of the image a doctor does not want to observe is also changed to be the same as the image being observed closely. In this case, despite that one image need not be observed closely, because of high scanning line density of this one image, the frame rate of another image is decreased. Furthermore, a display range of a monitor is limited and large display size of the one image limits the size of the other displayed image. In another word, the coupling of changing conditions of ultrasound images results in limitation of image quality and display size of an ultrasound image to be observed closely.

SUMMARY OF THE INVENTION

According to one aspect of the present invention, there is provided an ultrasound diagnostic apparatus and method for displaying ultrasound image in which the efficiency of three dimensional diagnosis is improved.

According to another aspect of the present invention there is provided an ultrasound diagnostic apparatus including a transmitting and receiving unit configured to transmit and receive ultrasound waves toward and from a plurality of planes of a subject by a ultrasonic probe, and a image signal generation unit configured to execute image processing on the basis of a received signal from the transmitting and receiving unit and to generate image signals for ultrasound images indicating each of the planes, wherein the transmitting and receiving unit or the image signal generation unit is configured to execute transmitting and receiving or image processing with respect to one of the planes in a condition that is different with respect to another of the planes.

According to a further aspect of the present invention there is provided a method for displaying ultrasonic image including transmitting and receiving ultrasound waves toward and from a plurality of planes of subject, and executing image processing on the basis of a received signal to generate image signals for ultrasound images indicating each of the planes, wherein a condition employed for the transmitting and receiving or the executing image processing with respect to one of the planes is different with respect to another of the planes.

DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Referring now to the drawings, wherein like reference numerals designate identical or corresponding parts throughout the several views, various embodiments of the present invention are next described.

(Components)

Figure 1:
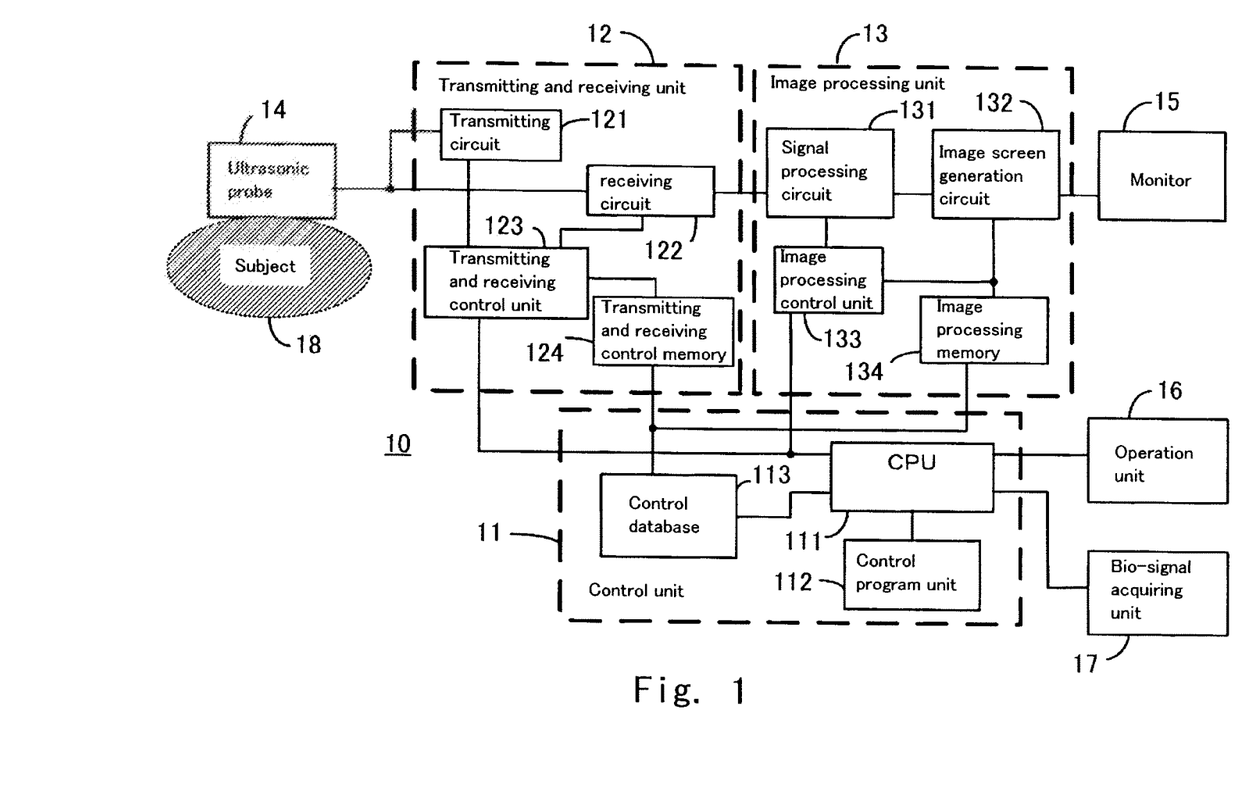
FIG. 1 is a block diagram of a exemplary embodiment of the ultrasonic diagnostic apparatus of the invention.

As shown in FIG. 1, an ultrasound diagnostic apparatus 10 of a exemplary embodiment includes a control unit 11, a transmitting and receiving unit 12, a signal processing unit 13, a two dimensional array probe 14, a monitor 15, an operation unit 16 including a key board, a track ball or a touch command screen (TCS) and a bio-signal acquiring unit 17.

The control unit 11 further includes a CPU 111, a control program unit 112 and a control database 113. The CPU 111 processes several kinds of signals. The control program unit 112 stores programs for processing of the CPU 111. The control database 113 stores data related to the multi scan plane function or multi display function.

The transmitting and receiving unit 12 further includes a transmit circuit 121, a receiving circuit 122, a transmitting and receiving control unit 123 and a transmitting and receiving control memory 124. The transmit circuit 121 transmits pulse signals for driving of the two dimensional array probe 14. The receiving circuit 122 processes ultrasound signals reflected from a subject 18. The transmitting and receiving control unit 123 controls the transmit circuit 121 and the receiving circuit 122 on the basis of control signals delivered from the CPU 111. The transmitting and receiving control memory 124 temporarily stores the transmitting and receiving control data from the control database 113.

The signal processing unit 13 further includes a signal processing circuit 131, an image processing memory 134, an image processing control unit 133, and a image screen generation unit 132. The signal processing circuit 131 processes signals delivered from the receiving circuit 122. The image processing memory 134 temporarily stores control data delivered from the control database 113. The signal image processing control unit 133 receives the control data delivered from the CPU 111 and the image control data memory 134 and transmits signal processing control signals to the signal processing circuit 131. The image screen generation circuit 132 converts the image signals from the signal processing circuit 131 into display screen data on the basis of control data from the image control data memory 134.

Figure 3A:
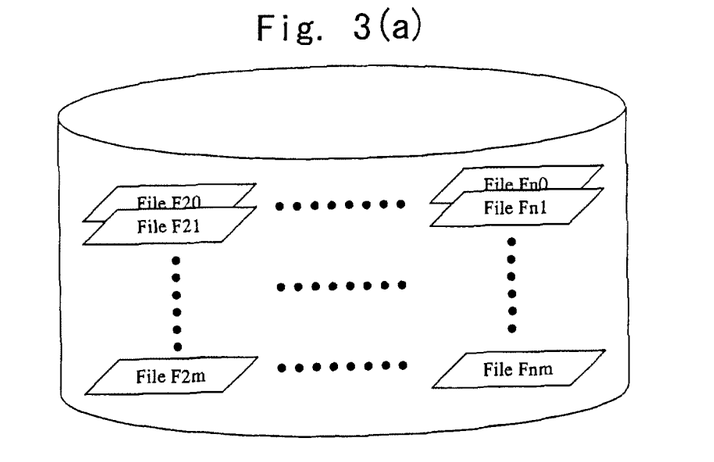
FIGS. 3(a) and 3(b) are illustrations of a frame format of components of files stored in a control database of the exemplary embodiment.
Figure 3B:
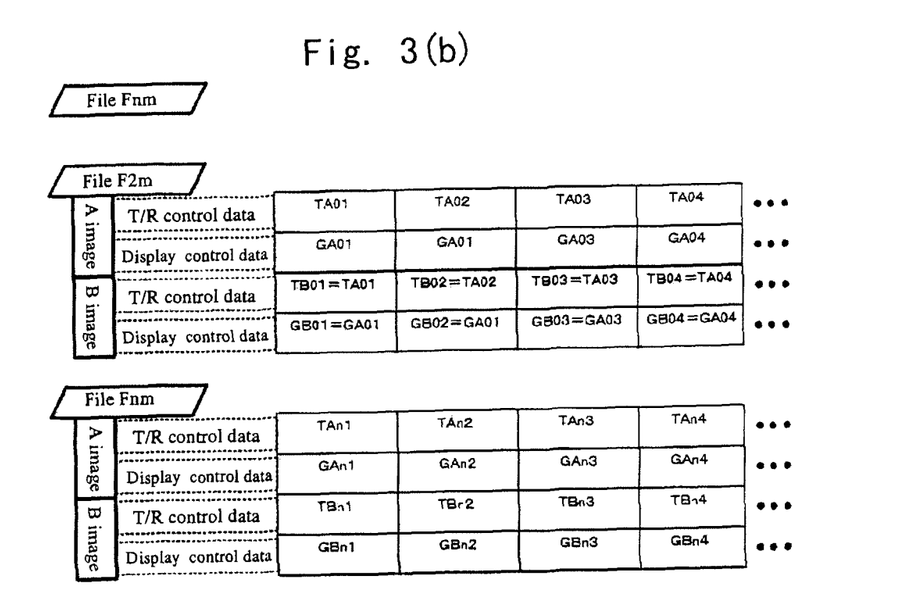

The control database 113 stores control files which include a file for each of constructions of ultrasound images of the multi display function. The control file is set for every number (n) of ultrasound images displayed in the monitor 15 at same time. For example, control data are set as follows: control data for two image displays, control data for three image display, control data for four image display . . . . Furthermore, when the number of displayed images is n, a plurality of display modes is set. For example, in the two image display mode, there are control data for displaying images in the same size and control data for displaying one small image and another big image and so on. In other words, when a number of display modes is m and a number of images is n, the control data is grouped into file Fnm. By way of example, content of file F20 is shown as FIG. 3(b), where the file F20 is a 0th control file for two image display. In this explanation, the two images displayed at same time are named A image and B image. Data is set for each of these images. The data for each is further grouped into transmitting and receiving control data and image display control data. For example, transmitting and receiving control data further includes data related to ultrasound driving power, scanning line density, receiving gain, pulse gate range, beam delay data, scan order and so on. For example, the image display control data further includes data related to brightness, range, display size, color/monochrome display, freeze/movie display and so on.

It is presupposed that 0th data for X image of mth display mode is indicated by TXmo. In this exemplary embodiment, default setting of the multi display function is a file Fn0. The file Fn0 is set the same as the hitherto known multi display mode for displaying a plurality of images in a same manner.

Figure 2:
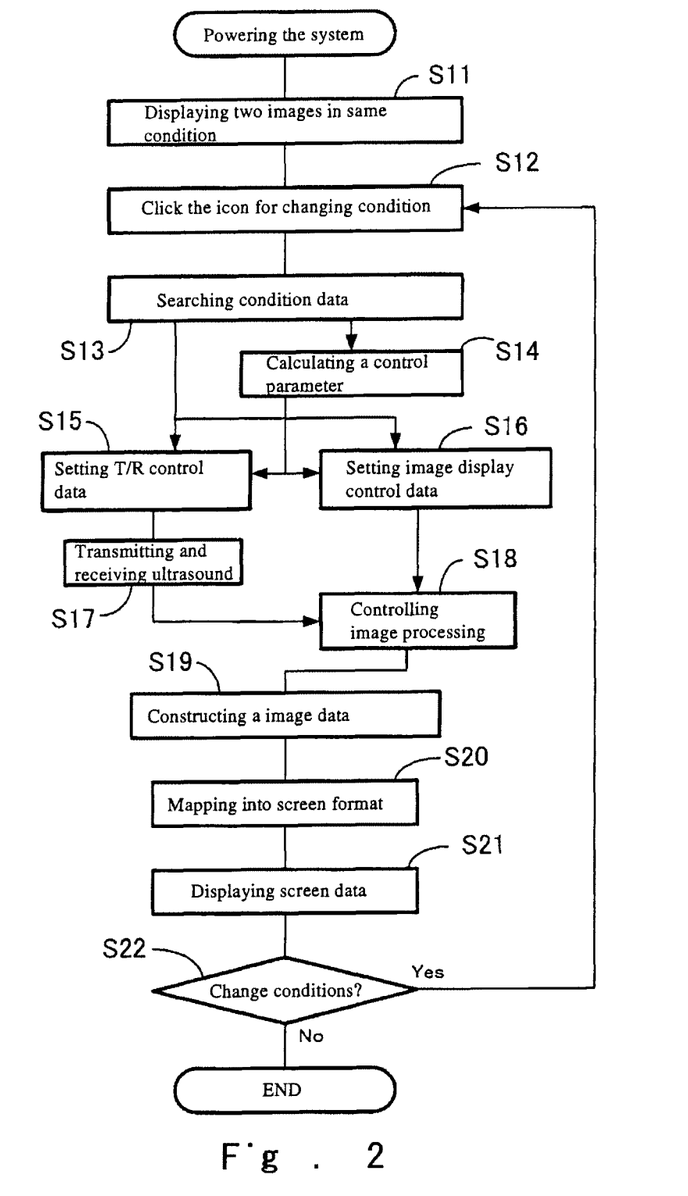
FIG. 2 is a flow chart of a processing by the ultrasonic diagnostic apparatus of the exemplary embodiment.

Next, an operation of the ultrasound diagnostic apparatus of this exemplary embodiment is explained by reference to FIG. 2. In the following explanation, it is presupposed that a number of images are displayed in same time. The images, which are the A image and the B image, are displayed side by side.

First, the ultrasound diagnostic apparatus of this exemplary embodiment is powered, and the display mode of two images display is selected by a predetermined operation. Next, in step S11, the A image and the B image are displayed in a same transmitting and receiving condition and image displaying condition. This is the same as the hitherto known multi display function. By observing these images, an operator searches for a portion of interest and finds a test portion of the subject in ultrasound image.

Next, the operator further closely observes and diagnoses. In step S12, the operator operates the TCS, the mouse, and the track ball of the operation input unit 16 in order to instruct a suitable ultrasound image display mode. By this instruction of step S12, in step S13, one of the files Fnm stored in the control database 113 is selected.

In step S15 transmitting and receiving control data for the selected file is temporarily stored in the transmitting and receiving control data memory 124. In step S16 signal processing control data of the selected file is temporarily stored in the image control data memory 134.

At the same time, a part of control data of the selected file Fnm is used as data for calculating control parameters in step S14. The calculated data is also temporarily stored in the transmitting and receiving control data memory 124 or the image control data memory 134.

On the basis of temporarily stored data in the transmitting and receiving control data memory 124, in step S17, the transmitting circuit 121 and the receiving circuit 122 are driven to transmit and receive ultrasound waves to and from the subject. In step S18, receiving signals processed in the receiving circuit 122 are inputted to the signal processing circuit 131. The signal processing circuit 131 generates image data for image display on the basis of control data for image display stored in the image control data memory 134.

The image data from the signal processing circuit 131 is inputted to the image screen generation circuit 132, which constructs a screen to be displayed in step S19. The construction of the screen is executed on the basis of the control data stored in the image control data memory 134. In step S20, according to setting by the step S19, picture elements of the A image and the B image are mapped into a screen frame memory in the image screen generation circuit 132.

Next, in step S21, the screen frame memory of the image screen generation circuit 132 is continuously read into the monitor 15. In this manner, the A image and the B image that have transmitting and receiving conditions and/or image display conditions different from each other are both displayed on the monitor 15.

Furthermore, in step S22, it is judged whether to change the transmitting and receiving conditions and image display conditions of the A image and the B image. In the case of changing the conditions, when instruction is inputted, the processing returns to step S12. In the case of not changing the conditions, the condition data of the file Fnm is maintained.

Furthermore, in this exemplary embodiment, the case of displaying two images is explained. However, in general three or more image display may be adapted in the above mentioned manner.

Next, examples of image display embodiments on the monitor 15 in this exemplary embodiment are described in reference to FIG. 4-FIG. 7. Here, the case that two images are displayed is explained.

(First Exemplary Display Embodiment)

Figure 4A:
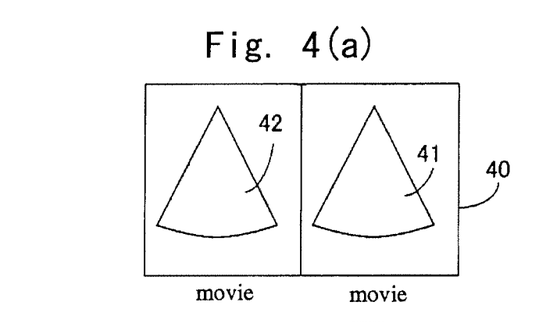
FIGS. 4(a) and 4(b) are illustrations of a frame format of the first exemplary display embodiment of the exemplary embodiment.
Figure 4B:
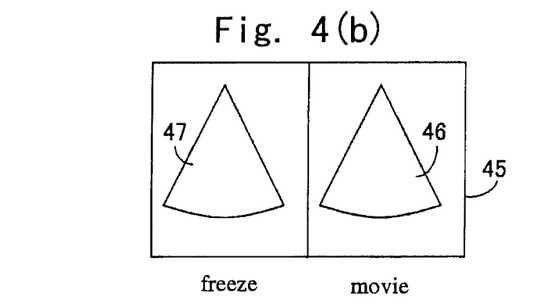

FIG. 4 shows an appearance of changing of display. In this exemplary display embodiment, an initial state is the same as the hitherto known appearance of the screen of the multi display function. The A image 41 and the B image 42 which indicate different planes are displayed in a same condition.

In this exemplary display embodiment, in step S12 an operator clicks an icon indicating selecting right image on TCS of the operation unit 16. This icon is for moving only the selected image.

This icon "selecting right" is corresponded to file F2a stored in the control database 113. In step S13, the file F2a is searched as condition data. Control data in the searched file F2a is described bellow. In transmitting and receiving control data for the A image, for parameter k=1 to k, data TAak and TBak is set so as to scan only for the A image. In other words, TAak is set preferably so as to scan only for the A image and TBak is set so as not to scan for the B image. GAak is set as a display condition according to TAak and GBak is set so as not to refresh the image and to be in the freeze state.

By this processing, image data are finally mapped in the image screen generation circuit 132. Therefore, screen data of each frame is delivered to the monitor 15. In this manner, as shown in FIG. 4(b), a right image 46 as a real time movie and a left image 47 as a freeze image of another plane are displayed on the monitor 15.

In this exemplary display embodiment, without waiting for scanning for the B image, only scanning for the A image is repeated. In this manner, frame rate of the A image is increased and an operator can observe a smooth image of the A image.

(Second Exemplary Display Embodiment)

Figure 5A:
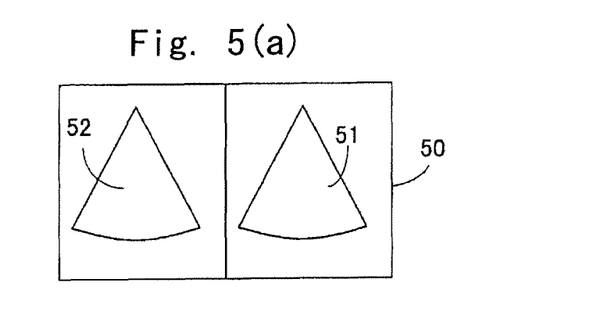
FIGS. 5(a) and 5(b) are illustrations of a frame format of the second exemplary display embodiment of the exemplary embodiment.
Figure 5B:
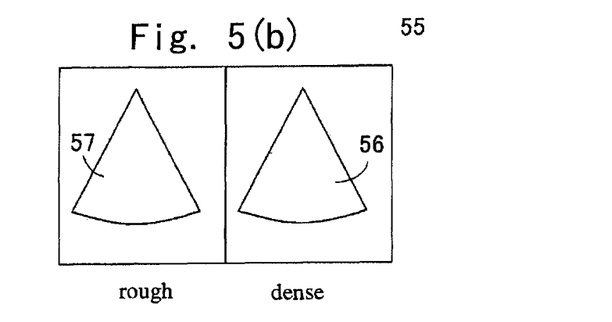

FIGS. 5(a) and 5(b) illustrate an appearance of changing of display. In this exemplary display embodiment, an initial state is the same as the hitherto known screen appearance of the multi display function. The A image 51 and the B image 52 which indicate different planes are displayed in a same condition.

In this exemplary display embodiment, in step S12 an operator clicks an icon indicating display advanced right image on TCS of the operation unit 16.

This icon "advancing right" is correlated to file F2b stored in the control database 113. In step S13, the file F2b is searched as condition data. In this file F2b, in item i indicating frame rate of image display control data, data is set as GA0i=GAbi, GB0i=GBbi. In other words, after changing display conditions, the same frame rate is maintained. On the other hand, in item h indicating density of scan line in transmitting and receiving control data, data is set as noted below. At first, in file F20 TA0h=TB0h, in an initial state, the A image and the B image are not distinguished. However, in file F2b for the changing, TA0h>TB0h. In other words, the displayed A image is denser than the displayed B image.

In step S15 and S16, this control data is delivered to the transmitting and receiving control unit 123 and the control unit 133. In this manner, without changing frame rate of the A image and the B image, scan line density of the A image is advanced and the B image is scanned successively.

By this processing, image data is finally mapped in the image screen generation circuit 132. Therefore, screen data of each frame are delivered to the monitor 15. In this manner, as shown in FIG. 4(b), a right image 46 as a real time movie and a left image 47 as a freeze image of another plane are displayed on the monitor 15. In this manner, an advanced A image and a deteriorating B image are displayed in real time on the monitor 15.

In this exemplary display embodiment, without stopping scanning of one image, another image can be advanced. An operator can understand three dimensional relationships by observing a plurality of images and observing one image closely.

In addition, in the above explanation, scan line density is changed and frame rate is maintained, but it is possible that frame rate is changed and scan line density is maintained. Also it is possible that frame rate and scan line density of one image are both advanced.

In the case that frame rate of one image is increased, the scan order for each plane is shown below. When the frame rate of the A image is increased, control data may be set so that the B image is scanned only once while the A image is scanned twice. For example, the A image is scanned while half of the B image is scanned. If scan line density is the same for each other, it is also possible that every two scan lines of the A image are transmitted and received while a scan line of the B image is transmitted and received.

In addition, a concrete value of scan line density may be set by an operator. Several values of scan line density may be set previously and an operator may be able to select from the several values. Known devices for inputting values may be provided and in accordance with the inputted values, scan line density may be set.

(Third Exemplary Display Embodiment)

Figure 6A:
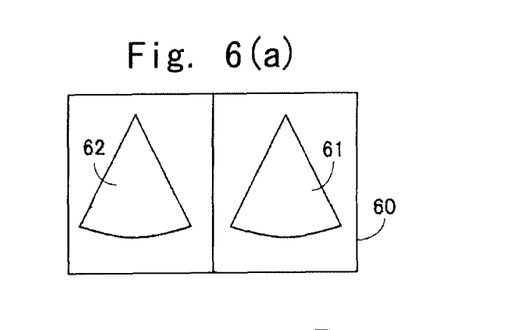
FIGS. 6(a) and 6(b) are illustrations of a frame format of the third exemplary display embodiment of the exemplary embodiment.
Figure 6B:
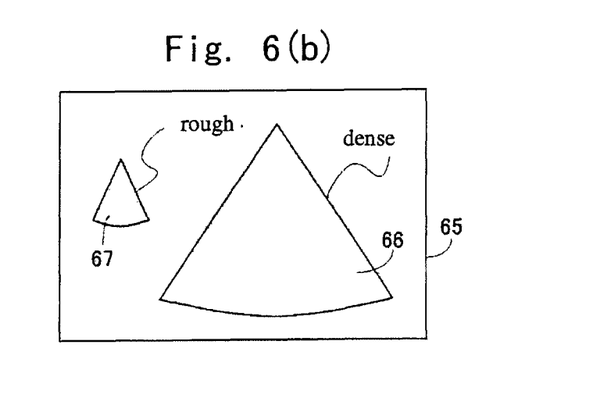

FIG. 6 shows an appearance of changing of display. In this exemplary display embodiment, an initial state is the same as the hitherto known screen appearance of the multi display function. The A image 61 and the B image 62 which indicate different planes are displayed in a same condition.

In this exemplary display embodiment, in step S12 an operator clicks an icon instructing to enlarge right image on TCS of the operation unit 16.

This icon "enlarge right" corresponds to file F2c stored in the control database 113. In step S13, the file F2c is searched as condition data. In this file F2c, TAch and TBch (TAch>TBch) are set as data for scan line density of transmitting and receiving data and GAci and GBci (GAci>GBci) are set as data for display size of image display control data.

In other hand, in item h indicating density of scan line in transmitting and receiving control data, data is set as noted below. At first, in file F20 TA0h=TB0h, in an initial state, the A image and the B image are not distinguished. However, in file F2c for the changing, data is set as TAch>TBch. In other words, the displayed A image is denser than the B image. In item i indicating display size of image display control data, data is set as noted below. In file F20 data is set as GA0i=GB0i. In an initial state, the A image and the B image are not distinguished. However, in file F2c for the changing, data is set as GAci>GBci. In other words, the displayed size of the A image is larger than the size of the B image.

By the control data set as above noted, ultrasound beams are transmitted and received and the screen image 65 is generated. In this manner, as shown in FIG. 6(b), the displayed A image is bigger than the B image and has a denser scan line than the B image. In addition, both images move in real time.

In this exemplary display embodiment, without stopping scanning one image, another image can be advanced. An operator can understand the three dimensional relationship by observing a plurality of images and observing one image closely.

In addition, in the above explanation, scan line density and display size are changed and frame rate is maintained, but it is possible that frame rate and display size are changed and scan line density is maintained. Also it is possible that frame rate and scan line density of one image are both advanced. A concrete method of this manner is almost same as above mentioned manner in the first exemplary display embodiment.

In addition, as a method of setting concrete values of scan line density and display size, several values of scan line density or display size may be set previously and an operator may be able to select from the several values. Known devices for inputting values may be provided and in the accordance with the inputted value, scan line density or display size may be set.

(Fourth Exemplary Display Embodiment)

Figures 7A, 7B, 7C:
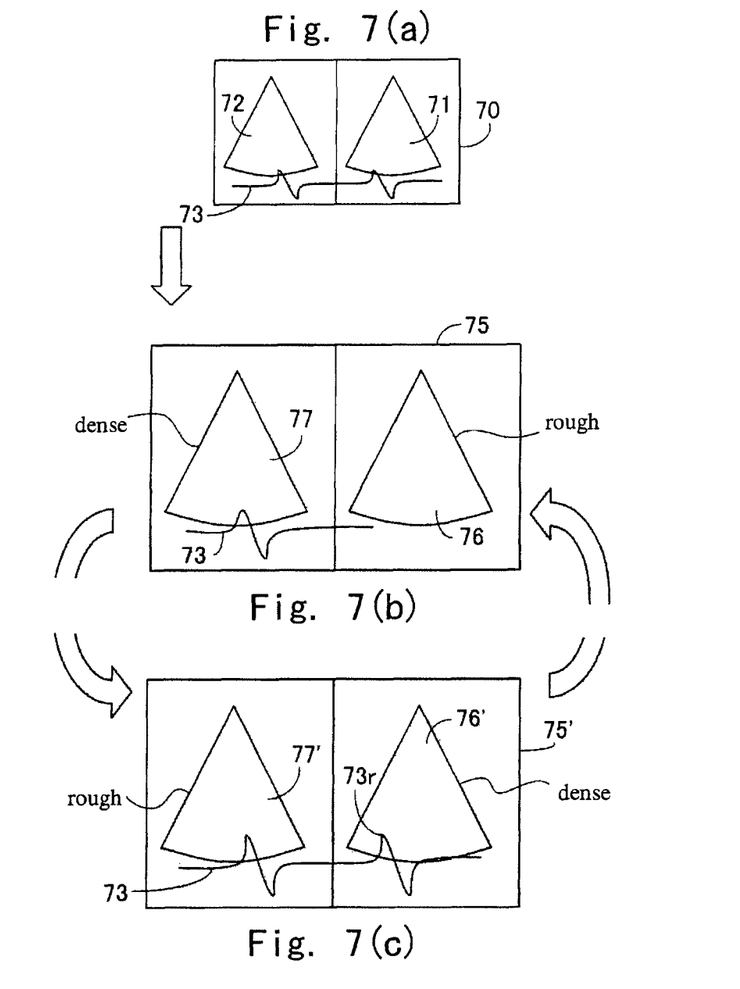
FIGS. 7(a), 7(b) and 7(c) are illustrations of a frame format of the forth exemplary display embodiment of the exemplary embodiment.

FIG. 7 illustrates an appearance of changing of display. In this exemplary display embodiment, an initial state is the same as the hitherto known screen appearance of the multi display function. The A image 71 and the B image 72 which indicate different planes are displayed in a same condition.

In addition, in this exemplary display embodiment, the bio-signal acquiring unit 17 is provided. The bio-signal may be one of an electro cardiograph (ECG) signal, a phonocardiogram (PCG) signal or a breathing signal. In this explanation, the bio-signal is an ECG signal, and a transesophageal multi plane probe is provided. The transesophageal multi plane probe images a longitudinal plane and a traverse plane of the heart in accordance with synchronization of the ECG signal. The ECG 73 is displayed on the monitor as FIG. 7(a).

In this exemplary display embodiment, in step S12, an operator clicks an icon indicating change alternately on TCS of the operation unit 16.

This icon "change alternately" corresponds to file F2d stored in the control database 113. In step S13, the file F2d is searched as condition data. In this file F2d, TAdk and TBdk (TAdk<TBdk) are set as data for scan line density of transmitting and receiving data and GAdk and GBdk (GAdk<GBdk) are set as data for display size of image display control data. At first, in accordance with this setting, the B image is bigger and high density.

When the R wave is detected, data for the A image and data for the B image in the transmitting and receiving control data memory 124 and the image control data memory 134 are switched and rewrite performed. In other words, TBdk is set as data for the A image and TAdk is set as data for the B image. This processing is done in step S13. By repeating step S13 to step S19, switching the display condition of the A image and the B image is repeated.

In this manner, in one cardiac cycle, an operator can observe one plane, and in next cardiac cycle, an operator can observe another plane without stopping scanning of the one plane.

In addition, the above explanation is for the case using a transesophageal multi plane probe, but it is needless to say that the case using another two dimensional arrayed probe operated by contacting from outside the body can be adapted to this technique. In the case of observing the heart, this manner is especially effective.

In addition, in the above explanation, scan line density and display size are changed and frame rate is maintained. However it is possible that frame rate and display are changed and scan line density is maintained. Also it is possible that frame rata, scan line density and display size of one image are both advanced. A concrete method of this manner is almost same as above mentioned manner in the first exemplary display embodiment.

In addition, as a method of setting concrete value of scan line density and display size, several values of scan line density or display size may be set previously and an operator may be able to select from the several values. Known devices for inputting values may be provided and in the accordance with the inputted value, scan line density or display size may be set.

Numerous modifications and variations of the present invention are possible in light of the above teachings. It is therefore to be understood that within the scope of the appended claims, the invention may be practiced otherwise than as specifically described herein.

The invention claimed is:

1. An ultrasound diagnostic apparatus, comprising:
   a transmitting and receiving unit configured to transmit and receive ultrasound waves toward and from at least first and second planes of a subject by an ultrasonic probe in accordance with first control data for the first plane and second control data for the second plane, which include respective transmitting and receiving control conditions for each plane;
   an image signal generation unit configured to execute image processing based on a signal received from the transmitting and receiving unit and to generate image signals for displaying, at a same time, ultrasound images indicating the first plane and the second plane, in accordance with image display control data that controls a display of the generated image signals; and
   a bio-signal acquiring unit configured to acquire a bio-signal of the subject,
   wherein the transmitting and receiving unit is configured to execute transmitting and receiving, respectively, with respect to the first plane and the second plane to be displayed at the same time based on, in addition to a respective orientation angle, width, and depth of each plane, the respective transmitting and receiving control conditions, at least one of the respective transmitting and receiving control conditions being different for each of the planes; and
   the transmitting and receiving unit is configured to swap the first control data for the second control data according to detection of a predetermined form of the acquired bio-signal, so that the first control data is used for the second plane and the second control data is used for the first plane.

2. The ultrasound diagnostic apparatus according to claim 1, further comprising:
   a control data setting unit configured to set respective control data including the image display control data and the transmitting and receiving control data, and to set the respective control data with respect to each of the planes,
   wherein the transmitting and receiving unit is configured to execute the transmitting and receiving based on the respective transmitting and receiving control data for each of the planes.

3. The ultrasound diagnostic apparatus according to claim 1, wherein:
   the respective transmitting and receiving control conditions of each plane include a scan line density condition.

4. The ultrasound diagnostic apparatus according to claim 2, further comprising:
   a storage unit configured to store a plurality of files composed of the respective control data; and
   a selecting unit configured to select a file from the plurality of files,
   wherein the control data setting unit is configured to set the selected file for the planes.

5. A method for displaying ultrasonic images, comprising:
   transmitting and receiving ultrasound waves toward and from at least first and second planes of a subject, in accordance with first control data for the first plane and second control data for the second plane, which include respective transmitting and receiving control conditions for each plane, each plane having a respective orientation angle, width, and depth;

executing image processing based on a received signal, including generating image signals for displaying, at a same time, ultrasound images indicating the first plane and the second plane, in accordance with image display control data that controls a display of the generated image signals; and acquiring a bio-signal of the subject, wherein at least one of the respective transmitting and receiving control conditions for the transmitting and receiving with respect to the first plane and the second plane to be displayed at the same time is different for each of the plurality of planes; and the transmitting and receiving step includes swapping the first control data for the second control data according to detection of a predetermined form of the acquired bio-signal so that the first control data is used for the second plane and the second control data is used for the first plane.

6. The method for displaying ultrasonic images according to claim 5, further comprising:

setting respective control data including the image display control data and the transmitting and receiving control data with respect to each of the planes, wherein the transmitting and receiving is executed on the basis of the respective transmitting and receiving control data set with respect to each of the planes.

7. The method for displaying ultrasonic images according to claim 5, wherein:

the respective transmitting and receiving control conditions of each plane include a scan line density condition.

8. The method for displaying ultrasonic images according to claim 6, further comprising;

storing a plurality of files including the respective control data; and selecting a file from the plurality of files, wherein the control data setting comprises setting the selected files for the plurality of planes.

9. The method of claim 5, further comprising:

displaying the first plane and the second plane at the same time.

10. The method of claim 5, wherein the image display control data includes one of brightness, range, color/monochrome display, and freeze/movie display.

11. The ultrasound diagnostic apparatus of claim 1, wherein the image display data includes a display size condition.

12. The ultrasound diagnostic apparatus of claim 1, wherein the respective transmitting and receiving control conditions of each plane include a scan order condition.

13. The ultrasound diagnostic apparatus of claim 1, wherein the respective transmitting and receiving control conditions of each plane include a frame rate condition.

14. The method of claim 5, wherein the image display data includes a display size condition.

15. The method of claim 5, wherein the respective transmitting and receiving control conditions of each plane include a scan order condition.

16. The method of claim 5, wherein the respective transmitting and receiving control conditions of each plane include a frame rate condition.

17. The method of claim 5, wherein the image display control data does not affect the step of transmitting and receiving the ultrasound waves.

* * * * *